United States Patent
Oh et al.

(10) Patent No.: US 9,759,814 B2
(45) Date of Patent: Sep. 12, 2017

(54) METHOD AND APPARATUS FOR GENERATING THREE-DIMENSIONAL (3D) IMAGE OF TARGET OBJECT

(71) Applicant: SAMSUNG MEDISON CO., LTD., Gangwon-Do (KR)

(72) Inventors: Dong-hoon Oh, Gangwon-do (KR); Dong-gyu Hyun, Gangwon-do (KR); Han-jun Kim, Gangwon-Do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 137 days.

(21) Appl. No.: 14/500,388

(22) Filed: Sep. 29, 2014

(65) Prior Publication Data
US 2015/0093005 A1    Apr. 2, 2015

(30) Foreign Application Priority Data

Sep. 30, 2013  (KR) ............... 10-2013-0116899
Jul. 8, 2014   (KR) ............... 10-2014-0085306

(51) Int. Cl.
| | |
|---|---|
| *G01S 15/89* | (2006.01) |
| *G01S 7/52* | (2006.01) |
| *A61B 6/00* | (2006.01) |
| *G06T 15/08* | (2011.01) |
| *G06T 15/50* | (2011.01) |
| *A61B 8/00* | (2006.01) |

(Continued)

(52) U.S. Cl.
CPC ........ *G01S 15/8993* (2013.01); *A61B 5/0035* (2013.01); *A61B 6/466* (2013.01); *A61B 8/466* (2013.01); *G01S 7/52068* (2013.01); *G06T 15/08* (2013.01); *G06T 15/50* (2013.01); *A61B 5/055* (2013.01); *A61B 5/7425* (2013.01); *G06T 2210/41* (2013.01)

(58) Field of Classification Search
CPC ......... A61B 1/00009; A61B 6/52; A61B 8/52; A61B 2576/00; A61B 2576/02; A61B 2576/023; A61B 5/1127; A61B 5/1128; G06T 7/0012; G06T 2207/10132; G06T 2207/10136; G06T 2207/30004; G06T 2207/03; G06K 2209/05; G06K 2209/051
USPC ............................................... 382/128
See application file for complete search history.

(56) References Cited

U.S. PATENT DOCUMENTS

2013/0150719 A1    6/2013  Orderud

FOREIGN PATENT DOCUMENTS

| EP | 2 208 467 A1 | 7/2010 |
| EP | 2 253 273 A1 | 11/2010 |

OTHER PUBLICATIONS

Binder, T. et al., "Three-Dimensional Imaging of the Heart Using Transesophageal Echocardiography," Proceedings of the Computers in Cardiology Conference. London, Sep. 5-8, 1993, Los Alamitos, IEEE Comp. Soc. Press, US, Sep. 5, 1993.

(Continued)

*Primary Examiner* — Bhavesh Mehta
*Assistant Examiner* — Narek Zohrabyan
(74) *Attorney, Agent, or Firm* — McDermott Will & Emery LLP

(57) ABSTRACT

A method of generating a three-dimensional (3D) image of a target object includes acquiring ultrasound data of the target object; and generating the 3D image of the target object by using the ultrasound data so that a part of the target object having attribute information different than attribute information of other parts of the target object is shown on the 3D image differently than the other parts.

8 Claims, 23 Drawing Sheets

(51) Int. Cl.
A61B 5/055 (2006.01)
A61B 5/00 (2006.01)

(56) References Cited

OTHER PUBLICATIONS

Extended European Search Report issued in corresponding European Patent Application No. 14182742.8, mailed on Mar. 23, 2015; 9 pages.

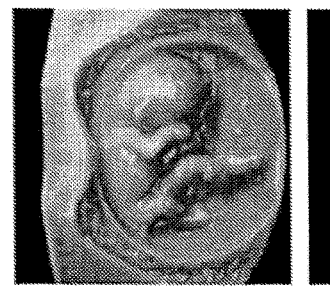 
FIG. 19A    FIG. 19B
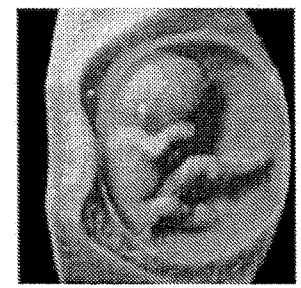 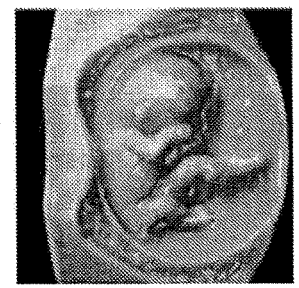
FIG. 20A    FIG. 20B

METHOD AND APPARATUS FOR GENERATING THREE-DIMENSIONAL (3D) IMAGE OF TARGET OBJECT

RELATED APPLICATIONS

This application claims the benefits of Korean Patent Application No. 10-2013-0116899, filed on Sep. 30, 2013, and Korean Patent Application No. 10-2014-0085306, filed on Jul. 8, 2014, in the Korean Intellectual Property Office, the disclosures of which are incorporated herein in their entireties by reference.

BACKGROUND

1. Field

One or more embodiments of the present invention relate to a method and apparatus for generating a three-dimensional (3D) image of a target object, and more particularly, to a method and apparatus for generating a 3D medical image of a target object.

2. Description of the Related Art

An ultrasound diagnosis apparatus transmits an ultrasonic signal from the surface of a body of a target object toward an inner part of the body by using a probe and obtains an image of a cross-section of soft tissue or a blood flow image by using information about an ultrasonic signal reflected by the inner part of the body.

The ultrasound diagnosis apparatus displays information about a target object in real time and is safe due to lack of exposure to X-rays or the like. Thus, such an ultrasound diagnosis apparatus is widely used together with other image diagnosis apparatuses, for example, an X-ray diagnosis apparatus, a computed tomography (CT) scanner, a magnetic resonance imaging (MRI) apparatus, a nuclear medical diagnosis apparatus, and the like.

SUMMARY

According to one or more embodiments of the present invention, a method of generating a three-dimensional (3D) image of a target object includes: acquiring ultrasound data of the target object; and generating the 3D image of the target object by using the ultrasound data, so that a part of the target object having attribute information different than attribute information of other parts of the target object is shown on the 3D image differently than the other parts.

The attribute information may include at least one selected from image attribute information, physical property information, and surface information of the target object.

The generating of the 3D image may be performed by using at least one selected from a specula reflection coefficient, a specular light exponent, and a color of the target object.

The generating of the 3D image of the target object may include performing rendering 3D image of the target object according to the attribute information.

The method may further include displaying the 3D image of the target object.

The generating of the 3D image of the target object may include generating an image having a reflection light effect.

The image having the reflection light effect may be generated by a plurality of light sources.

According to one or more embodiments of the present invention, an apparatus for generating a three-dimensional (3D) image of a target object includes: an ultrasound data acquirer which acquires ultrasound data of the target object; and an image generator which generates the 3D image of the target object by using the ultrasound data, so that a part of the target object having attribute information different than attribute information of other parts of the target object is shown on the 3D image differently than the other parts.

The attribute information may include at least one selected from image attribute information, physical property information, and surface information of the target object.

The image generator may generate the 3D image of the target object by using at least one selected from a specula reflection coefficient, a specular light exponent, and a color of the target object.

The image generator may generate the 3D image of the target object by performing rendering 3D image of the target object according to the attribute information.

The apparatus may further include a display unit which displays the 3D image of the target object.

The image generator may generate an image having a reflection light effect.

The image having the reflection light effect may be generated by a plurality of light sources.

According to one or more embodiments of the present invention, a method of generating a three-dimensional (3D) image of a target object includes: acquiring medical image data of the target object; and generating an image having a reflection light effect based on the medical image data.

The method may further include displaying the image having the reflection light effect.

The generating of the image having the reflection light effect may include: calculating a representative voxel to be displayed on a screen from among a plurality of voxels on a path of a view vector; calculating a surface normal vector; calculating a reflection light vector by using the surface normal vector; generating a color of the target object, a reflection coefficient for a light source, and a specular light exponent for the light source; and calculating a color of a single point in the image by using at least one selected from the reflection light vector, the color of the target object, the reflection coefficient for the light source, and the specular light exponent for the light source.

The generating of the image of the target object having the reflection light effect may include: extracting a depth map for the target object and screen; calculating a surface normal vector for the depth map; calculating a reflection light vector by using the surface normal vector; generating a color of the target object, a reflection coefficient for a light source, and a specular light exponent; and calculating a color of a single point in the image by using at least one selected from the reflection light vector, the color of the target object, the reflection coefficient for the light source, and the specular light exponent for the light source.

The image having the reflection light effect may be generated via a plurality of renderings including specular rendering.

The image having the reflection light effect may be generated by using a plurality of light sources.

The medical image data may be acquired by an ultrasound diagnosis apparatus, an X-ray diagnosis apparatus, a computed tomography (CT) scanner, or a magnetic resonance imaging (MRI) apparatus.

According to one or more embodiments of the present invention, an apparatus for generating a three-dimensional (3D) image of a target object includes: an ultrasound data acquirer which acquires medical image data of the target object; and an image generator which generates a three-dimensional (3D) image having a reflection light effect based on the medical image data.

The apparatus may further include a display unit which displays the image having the reflection light effect.

The image generator may receive from an external source a color of the target object, a reflection coefficient for a light source, and a specular light exponent for the light source or internally calculates the color of the target object, the reflection coefficient for the light source, and the specular light exponent for the light source, and calculates a color of a single point in the image by using at least one selected from the color of the target object, the reflection coefficient for the light source, and the specular light exponent for the light source.

The image generator may extract a depth map for the target object on a screen, calculates a reflection light vector, and calculates a color of a single point in the image by using the reflection light vector.

The image having the reflection light effect may be generated by a plurality of light sources.

The image having the reflection light effect may be generated via a plurality of renderings including specular rendering.

The medical image data may be acquired by an ultrasound diagnosis apparatus, an X-ray diagnosis apparatus, a computed tomography (CT) scanner, or a magnetic resonance imaging (MRI) apparatus.

BRIEF DESCRIPTION OF THE DRAWINGS

These and/or other aspects will become apparent and more readily appreciated from the following description of the embodiments, taken in conjunction with the accompanying drawings in which:

FIGS. 19A and 19B illustrate images in which different pieces of attribute information of a window area of a target object are respectively reflected according to specular light exponents, according to an embodiment of the present invention;

FIGS. 20A and 20B illustrate images in which different pieces of attribute information of a window area of a target object are respectively reflected according to specula reflection coefficients, according to an embodiment of the present invention;

DETAILED DESCRIPTION

Figure 1:
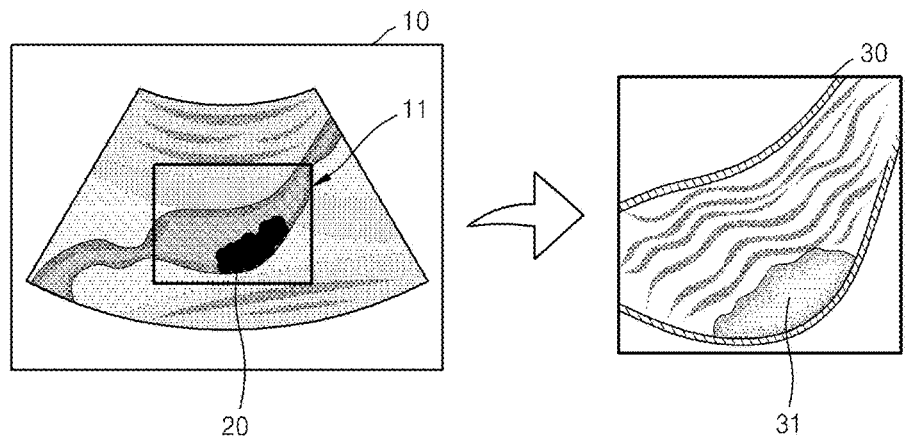
FIG. 1 illustrates an ultrasound image of a target object and a 3D rendered image thereof.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

The terminology used herein will be briefly described as the present invention will be described in detail based on this terminology.

Although general terms widely used at present were selected for describing the present invention in consideration of the functions thereof, these general terms may vary according to intentions of one of ordinary skill in the art, case precedents, the advent of new technologies, and the like. Terms arbitrarily selected by the applicant of the present invention may also be used in a specific case. In this case, their meanings need to be given in the detailed description of the present invention. Hence, the terms must be defined based on their meanings and the contents of the entire specification, not by simply stating the terms.

The terms "comprises" and/or "comprising" or "includes" and/or "including" when used in this specification, specify the presence of stated elements, but do not preclude the presence or addition of one or more other elements. The terms " . . . unit" and " . . . module", when used in this specification, refers to a unit in which at least one function or operation is performed, and may be implemented as hardware, software, or a combination of hardware and software.

Throughout the specification, an "ultrasound image" refers to an image of a target object which is obtained using ultrasound. The target object may be a part of a body. For example, the target object may be an organ (for example, the liver, the heart, the womb, the brain, a breast, or the abdomen), an embryo, or the like.

Throughout the specification, a "medical image" refers not only to an image of a target object that is obtained using ultrasound but also to an image of a target object that is captured by an X-ray diagnosis apparatus, a computed tomography (CT) scanner, a magnetic resonance imaging (MRI) apparatus, or a nuclear medical diagnosis apparatus.

Throughout the specification, a "user" may be, but is not limited to, a medical expert, such as a medic, a nurse, a medical laboratory technologist, a medical image expert, or the like.

Throughout the specification, a "voxel" may be, but is not limited to, a minimal unit of a three-dimensional (3D) image.

Embodiments of the present invention are described in detail herein with reference to the accompanying drawings so that this disclosure may be easily performed by one of ordinary skill in the art to which the present invention pertain. The invention may, however, be embodied in many different forms and should not be construed as being limited to the embodiments set forth herein. In the drawings, parts irrelevant to the description are omitted for simplicity of explanation, and like numbers refer to like elements throughout.

FIG. 1 illustrates an ultrasound image 10 of a target object and a 3D rendered image 30 thereof.

Until now, a 3D ultrasound technology has been used for fetal diagnosis. However, this technology has been developed into a technology capable of providing scans of various organs, such as a digestive organ, which are obtained by using an endoscope, without using an endoscope.

For example, when a 3D ultrasound technology is used, the internal structure of a digestive organ may be easily ascertained by using ultrasound data of the digestive organ including a stomach and the like and a 3D volume rendering technique, for example.

However, when such a 3D ultrasound technology is used, since 3D volume rendering is performed using only structural information shown on an ultrasound image of a target object, properties (for example, texture) of the target object may not be accurately expressed.

For example, as illustrated in FIG. 1, when a target object (for example, the stomach of a patient) includes a deposit 20 (for example, noodles attached to the stomach), the deposit 20 may be shown brighter than neighboring tissues on the ultrasound image 10 of the target object. When a certain area 11 is selected from the ultrasound image 10 for precise observation of the deposit 20 and rendering is performed with regard to the certain area 11, the deposit 20 within the target object may be shown like a polyp 31 on the 3D rendered image 30.

According to this method, since rendering is performed using only structural information of the target object without considering the properties of the deposit 20, a rendering error may occur and the deposit 20 may be shown as a polyp, thereby leading to wrong clinical judgment of a user.

The deposit 20 and the like may have a different brightness and a different texture than surrounding tissues on a two-dimensional (2D) ultrasound image of the target object. Thus, according to an embodiment of the present invention, 3D volume rendering is performed based on the attributes of the target object including the deposit 20 and the like to thereby provide a user with a 3D image in which the attributes of the target object are reflected.

According to an apparatus or method of generating a 3D image according to an embodiment of the present invention, when a 3D image of a target object is generated using acquired ultrasound data, the 3D image of the target object may be generated so that a part of the target object having attribute information different from other parts of the target object may be shown on the 3D image differently from the other parts. For example, when the deposit 20 has different attribute information than attribute information of neighboring tissues in FIG. 1, the deposit 20 may be shown differently from the neighboring tissues on a 3D image.

According to an apparatus or method of generating a 3D image according to an embodiment of the present invention, when pieces of ultrasound data of parts of a target object have different pieces of attribute information, the parts of object may be differently shown on the 3D image. Attribute information used in the present specification may include at least one selected from image attribute information, physical property information, and surface information. The attribute information will now be described in more detail.

Figure 2:
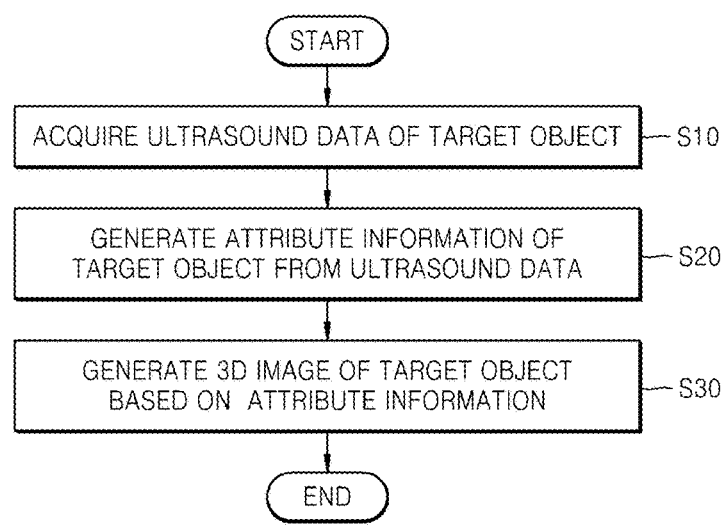
FIG. 2 is a flowchart of a method of generating a 3D image in which attribute information of a target object is reflected, according to an embodiment of the present invention.

FIG. 2 is a flowchart of a method of generating a 3D image in which attribute information of a target object is reflected, according to an embodiment of the present invention.

Referring to FIG. 2, the method may include operation S10 of acquiring ultrasound data of the target object, operation S20 of acquiring the attribute information of the target object from the ultrasound data, and operation S30 of generating the 3D image of the target object based on the attribute information.

The ultrasound data may include an ultrasound response signal received from the target object irradiated with ultrasound waves. The ultrasound response signal may include at least one selected from an analog signal and a digital signal.

For example, the ultrasound data may include an ultrasound response signal that is acquired from a target object and may be expressed in units of voxels. In other words, the ultrasound data may include the amplitude and phase values of a returning ultrasound wave that returns from the target object to a probe after ultrasound waves are transmitted toward the target object via the probe and pass through the target object.

The attribute information of the target object may include image attribute information, physical property information, and surface information of the target object.

The image attribute information may include at least one selected from pieces of attribute information of an ultrasound image of the target object, such as a spatial frequency, an image intensity, an image histogram, a co-occurrence matrix, a local binary pattern (LBP), and homogeneity.

The homogeneity of the target object denotes a degree of change of the size or shape of at least one particle included in the target object. For example, when the size or shape of at least one particle (or tissue) included in the target object is different from that of other particles (or tissues), the homogeneity of the target object is small or very low. On the other hand, when the size or shape of at least one particle (or tissue) included in the target object is identical to that of other particles (or tissues), the target object has very high homogeneity.

The physical property information of the target object may include information representing the physical properties of the target object, such as, strength, hardness, elasticity, plasticity, viscosity, density, ductile, brittleness, malleability, rigidity, and toughness.

The surface information of the target object may include information representing a surface property of the target object that can be perceived via a tactile perception organ of a human, such as, 'smooth', 'bumpy', 'rough', and 'soft'.

The surface information of the target object may also include information representing a visual or three-dimensional property of the target object that can be perceived via a visual organ of a human, such as, 'a contrast between brightness and darkness', 'separation or division between the entire background and a predetermined product.

The attribute information of the target object may be information about each of a plurality of pixels that constitute an image of the target object, or information about each of at least one area that constitutes the image of the target object. The attribute information of the target object may also be information about a frame of the image of the target object.

The ultrasound image of the target object may be at least one selected from a brightness (B) mode image, a color (C) mode image, and a Doppler (D) mode image. According to an embodiment of the present invention, the ultrasound image may be a 2D or 3D image of the target object.

The operation S20 of acquiring the attribute information of the target object from the ultrasound data may include an operation of acquiring a spatial frequency, an image intensity, an image histogram, a co-occurrence matrix, an LBP, or homogeneity based on the ultrasound image generated according to the ultrasound response signal.

The operation S20 of acquiring the attribute information of the target object from the ultrasound data may include an operation of analyzing the image attribute information of the target object and an operation of determining the attribute information of the target object based on a result of the analysis.

The analysis of the image attribute information and the determination of the attribute information will now be described in detail with reference to FIGS. 3-8.

Figure 3:
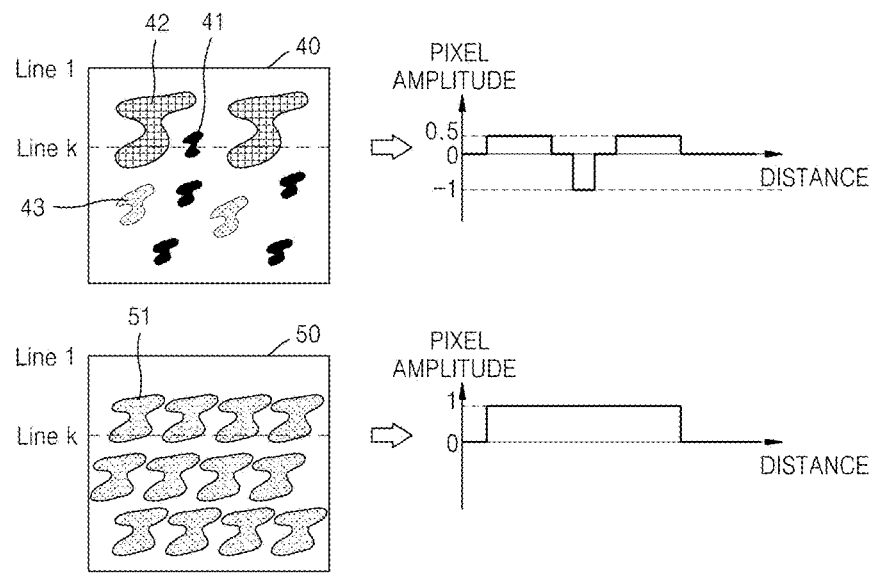
FIG. 3 illustrates a case where image attribute information of a target object is a spatial frequency, according to an embodiment of the present invention.

FIG. 3 illustrates a case where the image attribute information of a target object is a spatial frequency, according to an embodiment of the present invention.

A spatial frequency represents a rate at which a pixel value varies in a horizontal or vertical direction on a screen on which an image is shown. For example, when a pixel value changes slowly (or when a pixel value remain almost unchanged) or a correlation between objects included in an image is high, a spatial frequency is low. On the other hand, when a pixel value varies greatly (or when a pixel value changes discontinuously like an edge) or a correlation between objects included in an image is low, a spatial frequency is high.

A first or second ultrasound image 40 or 50 of the target object may be acquired as illustrated in FIG. 3. The first or second ultrasound image 40 or 50 of the target object may be a portion of the ultrasound image 10 of the target object (for example, a portion of the ultrasound image 10 corresponding to a selected area 11 of FIG. 1).

For example, sizes of tissues 41, 42, and 43 of the target object may be different from one another. The term tissue used in the present specification may refer to a particle of an organ of a target object or a particle of a deposit. The target object may include the tissue 42, which has the largest size, the tissue 43, which has a medium size, and the tissue 41, which has the smallest size. Shapes of the tissues 41, 42, and 43 of the target object may also be different from one another.

Brightness values of the tissues 41, 42, and 43 of the target object may also be different from one another. For example, the target object may include the tissue 43, which is the brightest on the first or second ultrasound image 40 or 50, the tissue 42, which is moderately bright on the first or second ultrasound image 40 or 50, and the tissue 41, which is the darkest on the first or second ultrasound image 40 or 50. Since different ultrasound response signals may be generated according to the depths, densities, elasticity, and the like of tissues, different tissues have different brightness values. For example, the tissue 41, which is located at the highest depth from among the tissues 41, 42, and 43, may be the darkest tissue on the first or second ultrasound image 40 or 50. In other words, as the depth of the tissue increase, the brightness value thereof may decrease.

The brightness values of a plurality of pixels on a line k located at a k-th position from the top of the first ultrasound image 40 may be expressed as the amplitude values of the pixels as illustrated in FIG. 3. For example, the tissue 42, which is moderately bright, may be expressed as a pixel amplitude value of 0.5. The tissue 41, which is the darkest, may be expressed as a pixel amplitude value of −1.

To correspond to the first ultrasound image 40, the brightness values of a plurality of pixels on a line k located at a k-th position from the top of the second ultrasound image 50 may also be expressed as the amplitude values of the pixels as illustrated in FIG. 3. The second ultrasound image 50 includes tissues 51 having identical sizes and identical brightness values. Accordingly, as illustrated in FIG. 3, the brightness values of the pixels on the line k on the second ultrasound image 50 may be all expressed as a pixel amplitude value of 1.

The first ultrasound image 40 and the second ultrasound image 50 are characterized by different aspects in terms of the brightness values of a plurality of pixels in the same k-th line. In other words, a pixel amplitude value (or a pixel brightness value) of the first ultrasound image 40 variously changes from −1 to 0.5, whereas a pixel amplitude value of the second ultrasound image 50 only changes from 0 to 1.

In the aforementioned example, since a pixel amplitude value of the first ultrasound image 40 varies greatly, the spatial frequency of the first ultrasound image 40 may be determined to be high. In other words, correlations between the tissues 41, 42, and 43 included in the first ultrasound image 40 are low, and thus the target object corresponding to the first ultrasound image 40 may be determined to have a 'bumpy' or 'rough' property.

Since the pixel amplitude value of the second ultrasound image 50 remains almost unchanged compared with the first ultrasound image 40, the spatial frequency of the second ultrasound image 50 may be determined to be low. In other words, correlations between the objects (for example, the tissues 51) included in the second ultrasound image 50 are very high, and thus the target object corresponding to the second ultrasound image 50 may be determined to have a 'smooth' or 'soft' property.

As described above, the spatial frequency of an ultrasound image of a target object may be extracted as image attribute information of the target object, and attribute information of the target object may be determined (or acquired) based on the spatial frequency.

Figure 4:
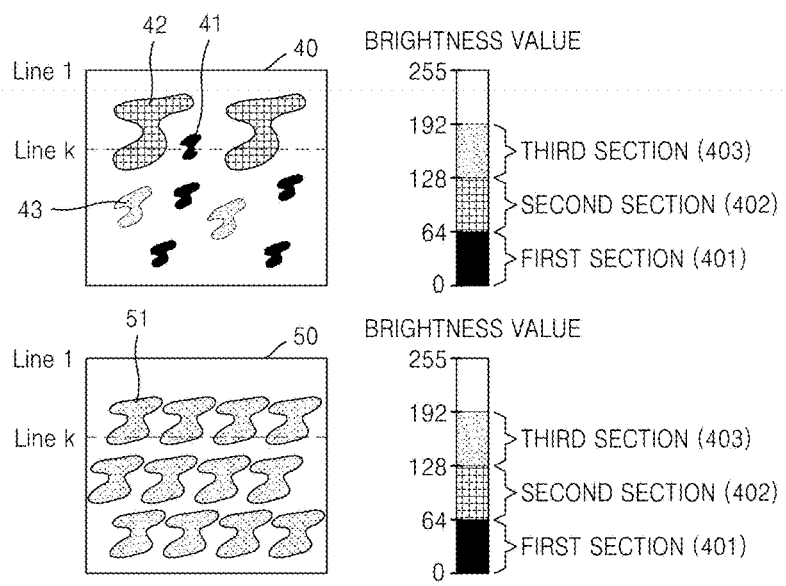
FIG. 4 illustrates a case where the image attribute information is image intensity, according to an embodiment of the present invention.

FIG. 4 illustrates a case where the image attribute information is image intensity, according to an embodiment of the present invention.

An image intensity according to an embodiment of the present invention may be expressed as the brightness values of a plurality of pixels of an ultrasound image of a target object.

As illustrated in FIG. 4, a plurality of tissues 41 through 43 having brightness values in different ranges (for example, first through third sections 401 through 403) may be shown on the first ultrasound image 40. Tissues 51 having brightness values in the same range (for example, the third section 403) may be shown on the second ultrasound image 50.

In other words, since the first ultrasound image 40 includes the tissue 41 having a brightness value in the first section 401 (for example, a dark section), the tissue 42 having a brightness value in the second section 402 (for example, a middle-brightness section), and the tissue 43 having a brightness value in the third section 403 (for example, a bright section), the tissues 41 through 43 in the first ultrasound image 40 may be determined to be of different types. Even when the tissues 41 through 43 are of the same kind, the brightness values of the tissues 41 through 43 are in different brightness sections, and thus the tissues 41 through 43 may be determined to be located at different depths.

Accordingly, the target object corresponding to the first ultrasound image 40 may be determined to have a 'bumpy' or 'rough' property.

On the other hand, since the second ultrasound image 50 includes the tissues 51 having all brightness values in the third section 403 (for example, a bright section), the tissues 51 of the second ultrasound image 50 may be determined to be of the same kind.

Accordingly, the target object corresponding to the second ultrasound image 50 may be determined to have a 'smooth' or 'soft' property.

Figure 5:
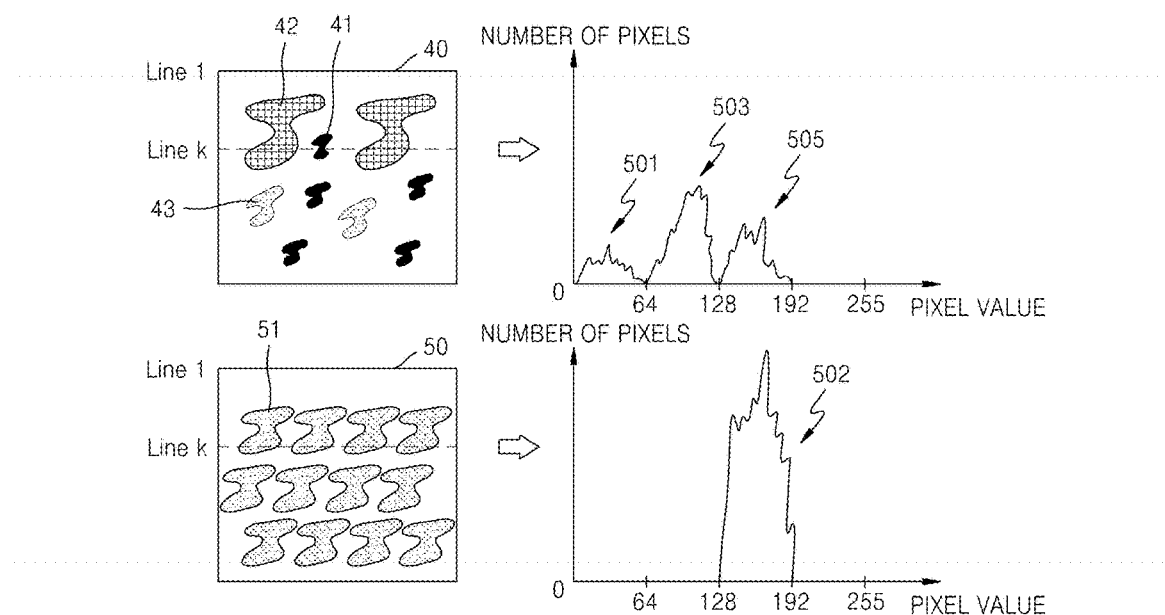
FIG. 5 illustrates a case where the image attribute information is an image histogram, according to an embodiment of the present invention.

FIG. 5 illustrates a case where the image attribute information is an image histogram, according to an embodiment of the present invention.

An image histogram of the first or second ultrasound image 40 or 50 may be acquired as the image attribute information as illustrated in FIG. 5.

The image histogram of the first or second ultrasound image 40 or 50 represents the number of pixels versus pixel values (for example, brightness values) of the first or second ultrasound image 40 or 50.

As in FIG. 5, the tissues 41 through 43 having different brightness values may be shown in the first ultrasound image 40. The numbers of pixels of the tissues 41 through 43 of the first ultrasound image 40 versus pixel values thereof may be evenly distributed between a pixel value of 0 and a pixel value of 192.

Referring to FIGS. 4 and 5, in the image histogram, the number of pixels having brightness values in the first section 401 may be represented as a first graph 501, the number of pixels having brightness values in the second section 402 may be represented as a second graph 402, and the number of pixels having brightness values in the third section 403 may be represented as a third graph 505.

Thus, the tissues 41 through 43 included in the first ultrasound image 40 may be determined to be of different types having various brightness values. Even when the tissues 41 through 43 are of the same kind, a histogram distribution of the tissues 41 through 43 is relatively wide, and thus the tissues 41 through 43 may be determined to be located at different depths.

Accordingly, the target object corresponding to the first ultrasound image 40 may be determined to have a 'bumpy' or 'rough' property.

Tissues 51 having the same or similar brightness values may be shown in the second ultrasound image 50. Referring to FIGS. 4 and 5, since only the number of pixels having brightness values in the third section 403 may be represented as a fourth graph 502 on the image histogram of the second ultrasound image 50, the second ultrasound image 50 may be determined to include the tissues 51 of the same kind.

Accordingly, the target object corresponding to the second ultrasound image 50 may be determined to have a 'smooth' or 'soft' property.

Figure 6:
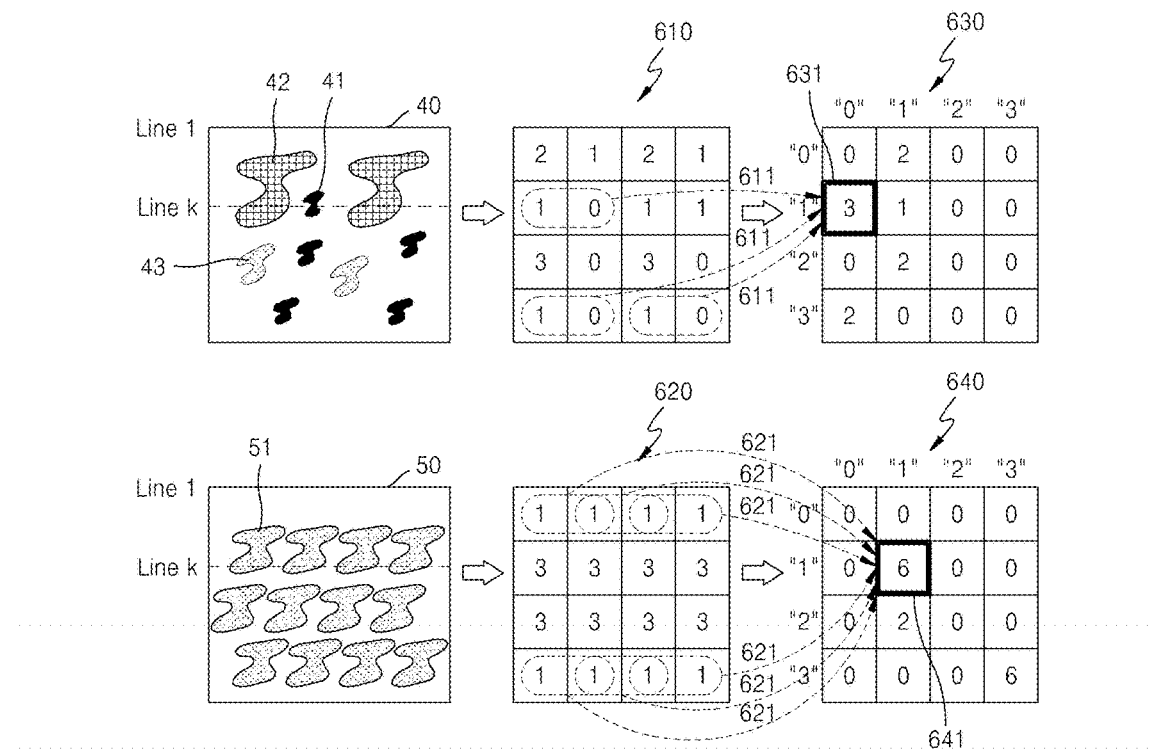
FIG. 6 illustrates a case where the image attribute information is a co-concurrence matrix, according to an embodiment of the present invention.

FIG. 6 illustrates a case where the image attribute information is a co-concurrence matrix, according to an embodiment of the present invention.

The co-occurrence matrix may be used to determine repeatability of pixel values. For example, when many values correspond to a predetermined pattern, repetitiveness of this pattern may be determined to be high.

For convenience of explanation, as illustrated in FIG. 6, when respective brightness values of the tissue 43, which is the brightest, the tissue 42, which is moderately bright, and the tissue 41, which is the darkest, are represented as 3, 2, and 0, respectively, the first ultrasound image 40 may be simply represented as a 4×4 matrix 610 which represents the pixel values of the first ultrasound image 40.

A co-occurrence matrix 630 may be acquired using a pattern indicated in units of an inter-pixel horizontal distance of 1 with respect to the 4×4 matrix 610. However, the inter-pixel direction of the pattern indication is not limited to a horizontal direction, and the pattern indication may be performed in a vertical direction, a diagonal direction, or the like.

For example, when pixel values exist side by side in a horizontal pattern of (1, 0) as indicated by reference numeral 611, the number of horizontal patterns of (1, 0), namely, 3, is shown on an element 631 of the co-concurrence matrix 630 that corresponds to a pattern of (1, 0). Each element of a matrix is represented by the number of patterns corresponding thereto to thereby acquire the co-occurrence matrix 630.

By expressing the brightness values of the tissues 51 included in the second ultrasound image 50 as 3, the second ultrasound image 50 may also be represented as a 4×4 matrix 620. A co-occurrence matrix 640 for the second ultrasound image 50 may be acquired in the same manner as the co-occurrence matrix 630 for the first ultrasound image 40.

In the co-occurrence matrix 640 for the second ultrasound image 50, the value of a specific element 641 is overwhelmingly high. In other words, since a pattern of (1, 1) is repeated six times on the second ultrasound image 50, the element 641 corresponding to the pattern of (1, 1) may be expressed as 6.

Compared with the co-occurrence matrix 630 for the first ultrasound image 40, the value of a specific element of the co-occurrence matrix 640 for the second ultrasound image 50 is overwhelmingly high, and thus the co-occurrence matrix 640 is relatively monotonous. The reason for this monotony is that a predetermined pattern (for example, (1, 1) or (3, 3)) is highly repeated on the second ultrasound image 50.

Since the second ultrasound image 50 has high pattern repetitiveness, the target object corresponding to the second ultrasound image 50 may be determined to have a 'smooth' or 'soft' property compared with that corresponding to the first ultrasound image 40.

Figure 7:
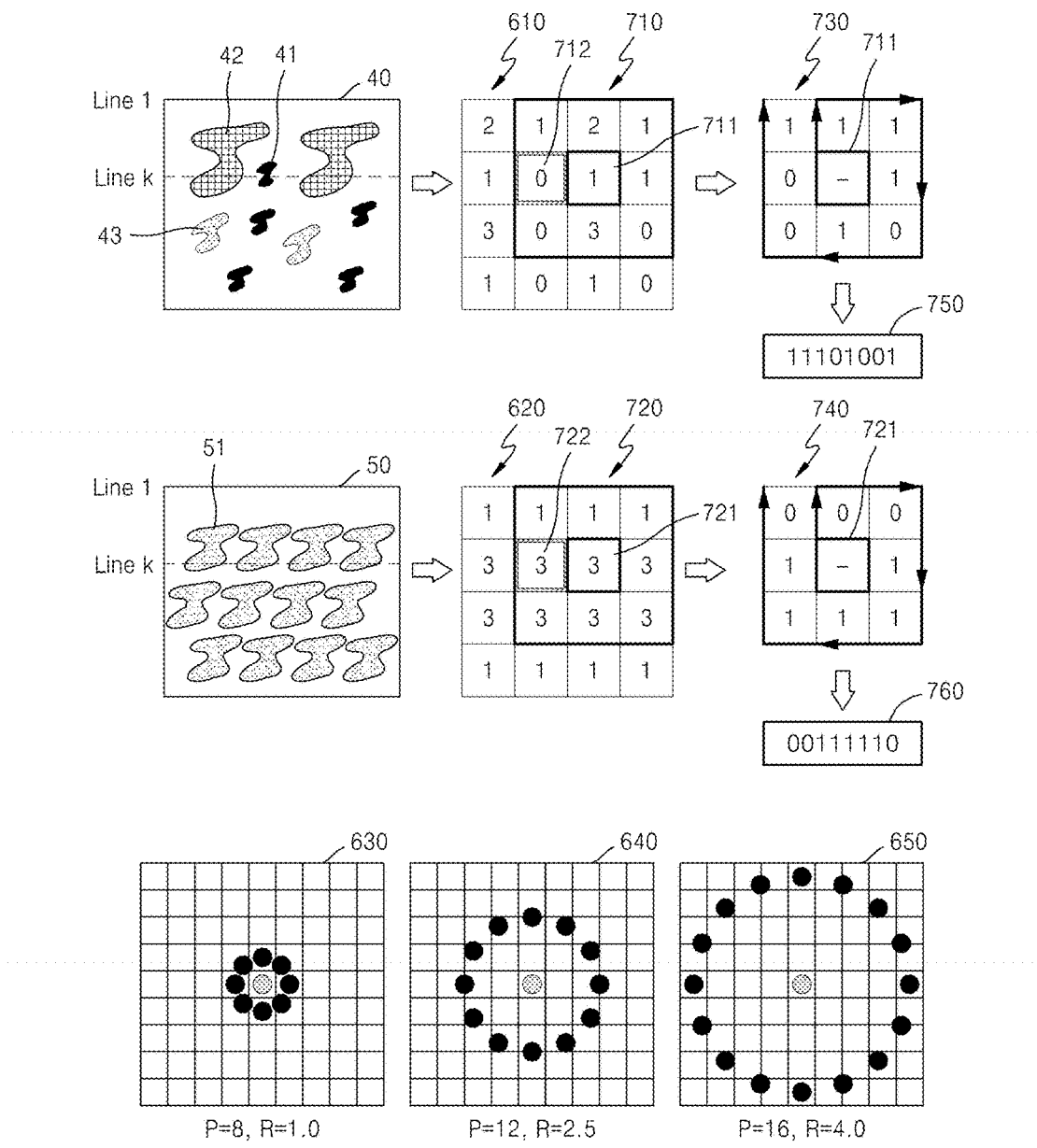
FIG. 7 illustrates a case where the image attribute information is a local binary pattern (LBP), according to an embodiment of the present invention.

FIG. 7 illustrates a case where the image attribute information is an LBP, according to an embodiment of the present invention.

The LBP is a technique for determining similarity between pixels by expressing a difference between a pixel value at a current position and a neighboring pixel in a binary system. In other words, the similarity between pixels may be determined by acquiring an LBP histogram in which a difference between each pixel of an image and each neighboring pixel within a predetermine radius is expressed as a binary value and by comparing a plurality of binary values obtained for each pixel with one another.

If the similarity between pixels is large, the pixels have the same feature. For example, pixels that are highly similar to each other may have the same or similar brightness values. Thus, patterns of an image may be relatively accurately predicted using an LBP.

As illustrated in FIG. 7, a 3×3 matrix 710 having an element 711 at the center thereof is selected from the 4×4 matrix 610, which represents the pixel values of the first ultrasound image 40. A neighboring pixel of which pixel value is equal to or higher than 1, namely, the pixel value of the element 711, is expressed as 1, and a neighboring pixel of which pixel value is lower than 1 is expressed as 0, thereby determining a binary expression matrix 730. The values of the elements of the binary expression matrix 730 may be interpreted clockwise starting from the element 711 to thereby obtain a binary value 750 of '11101001'. In this way, a binary value of '11111111' may be determined by starting from an element 712.

A binary value 760 of '00111110' may be acquired based on a 3×3 matrix 720 having an element 721 at the center thereof selected from the 4×4 matrix 620, which represents the pixel value of the second ultrasound image 50. In this way, a binary value of '00111110' may be acquired for an element 722.

The binary values of '11101001' and '11111111' determined from the first ultrasound image 40 are greatly different, but the binary values of '00111110' and '00111110' determined from the second ultrasound image 50 have no difference therebetween. In other words, an inter-pixel pixel value of the second ultrasound image 50 does not greatly change compared with the first ultrasound image 40.

Since an inter-pixel pixel value of the second ultrasound image 50 changes a little, the target object corresponding to the second ultrasound image 50 may be determined to have a 'smooth' or 'soft' property compared with the first ultrasound image 40.

Figure 8:
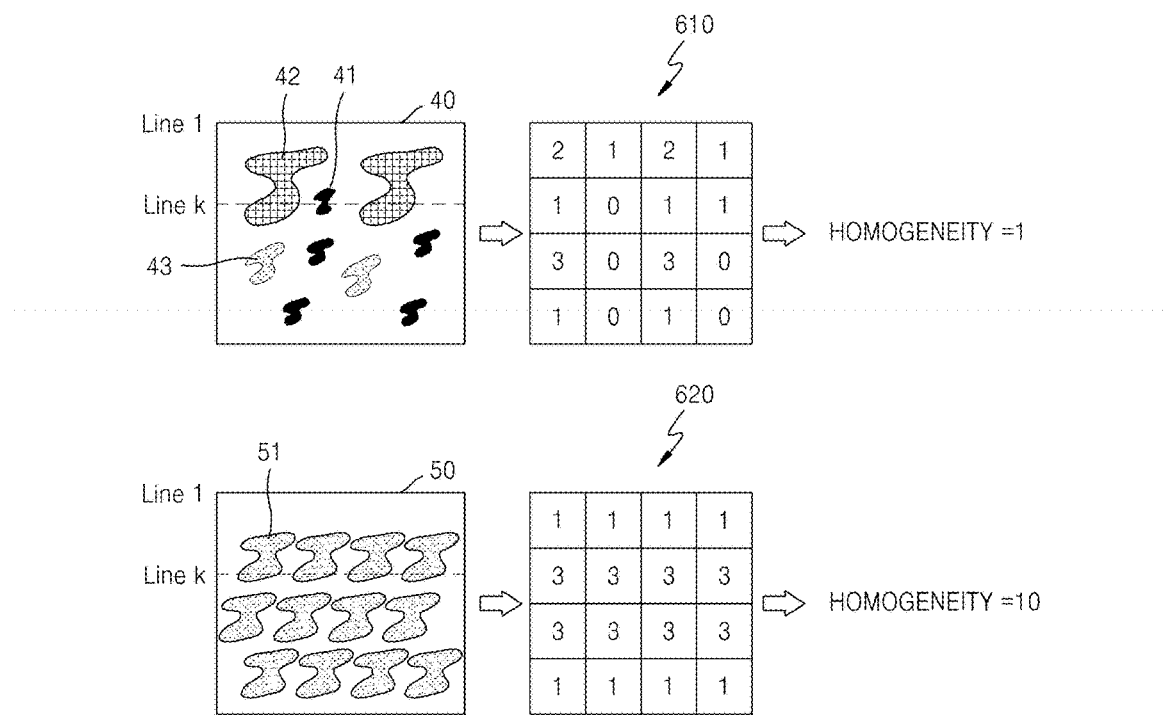
FIG. 8 illustrates a case where the image attribute information is homogeneity, according to an embodiment of the present invention.

FIG. 8 illustrates a case where the image attribute information is homogeneity, according to an embodiment of the present invention.

The homogeneity denotes homogeneity of the sizes or shapes of the tissue 41, 42, 43, and 51 in the first or second ultrasound image 40 or 50. For convenience of explanation, it is assumed that a homogeneity value corresponding to complete homogeneity is expressed as '10' and a homogeneity value when the sizes or shapes of tissues are not homogeneous is expressed as '1'.

The first ultrasound image 40 includes a plurality of tissues 41 through 43 having different sizes. Accordingly, the homogeneity of the first ultrasound image 40 may be determined to be low. For example, the homogeneity of the first ultrasound image 40 may be expressed as '1', and a particle (or tissue) included in the target object corresponding to the first ultrasound image 40 may be determined to be uneven. In other words, the target object corresponding to the first ultrasound image 40 may be determined to have a 'bumpy' or 'rough' property.

Compared to the first ultrasound image 40, the second ultrasound image 50 includes a plurality of tissues 51 having the same size. Accordingly, the homogeneity of the second ultrasound image 50 may be determined to be relatively high, compared with the first ultrasound image 40. For example, the homogeneity of the second ultrasound image 50 may be expressed as '10', and a particle (or tissue) included in the target object corresponding to the second ultrasound image 50 may be determined to be even. In other words, the target object corresponding to the second ultrasound image 50 may be determined to have a 'smooth' or 'soft' property, compared with the target object corresponding to the first ultrasound image 40.

Figure 9:
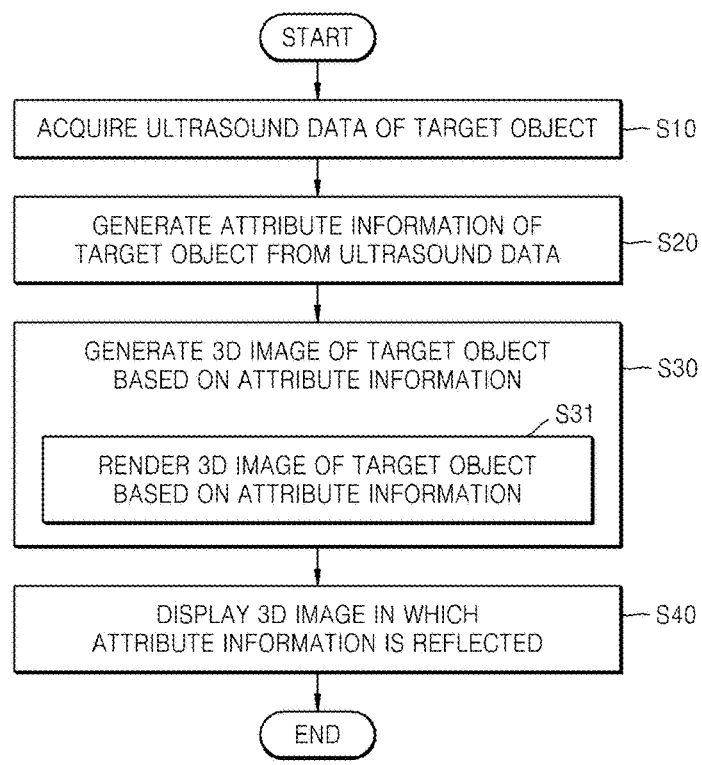
FIG. 9 is a flowchart of a method of displaying a 3D image which is generated by rendering and in which attribute information of a target object is reflected, according to an embodiment of the present invention.

FIG. 9 is a flowchart of a method of displaying and rendering a 3D image in which attribute information of a target object is reflected, according to an embodiment of the present invention.

In the present embodiment, operation S30 of generating the 3D image of the target object based on the attribute information may include operation S31 of rendering the 3D image of the target object based on the attribute information.

For example, the 3D image may be rendered using the attribute information generated according to the aforementioned method on the target object. In other words, when 3D volume rendering is performed on the target object, a 3D volume image in which not only a structure of the target object but also attributes of the target object, such as a texture of the target object, are reflected may be constructed using attribute (for example, a texture) information corresponding to each pixel, which is acquired (or determined) via the above-described analysis of the image attribute information.

The method according to the present embodiment may further include operation S40 of displaying the 3D image in which the attribute information is reflected.

Figure 10:
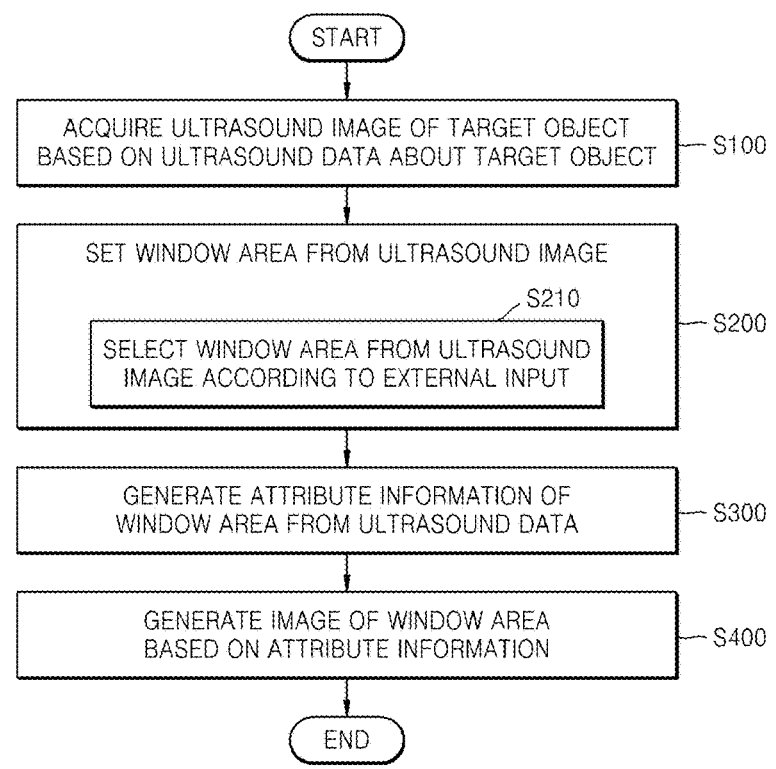
FIG. 10 is a flowchart of a method of generating an image in which attribute information of a window area of a target object is reflected, according to an embodiment of the present invention.

FIG. 10 is a flowchart of a method of generating an image in which attribute information of a window area of a target object is reflected, according to an embodiment of the present invention.

Referring to FIG. 10, the method may include operation S100 of acquiring an ultrasound image of the target object based on ultrasound data about the target object, operation S200 of setting the window area from the ultrasound image, operation S300 of generating attribute information of the window area from the ultrasound data, and operation S400 of generating an image of the window area based on the attribute information.

Operation S200 of setting the window area from the ultrasound image may include operation S210 of selecting the window area from the ultrasound image according to an external input.

The window area may be automatically set to have a predetermined size to include a predetermined part of the target object, although there are no external inputs. For example, a predetermined window area having a predetermined size may be automatically set to include an upper part or a bottom curved side of the stomach of a patient.

Image attribute information according to an embodiment of the present invention may include at least one selected from a spatial frequency, image intensity, an image histogram, a co-occurrence matrix, an LBP, and homogeneity of an ultrasound image of a target object, and the attribute information may include a texture of the target object.

Figure 11:
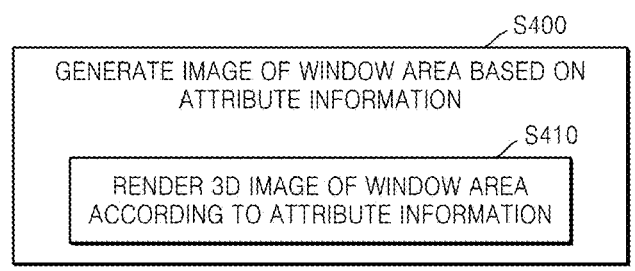
FIG. 11 is a flowchart of an operation of generating the image of the window area based on the attribute information according to an embodiment of the present invention.

FIG. 11 is a flowchart of an operation of generating the image of the window area based on the attribute information, according to an embodiment of the present invention.

In the present embodiment, the operation S400 may include operation S410 of rendering the 3D image of the window area according to the attribute information.

As described above, when 3D volume rendering is performed on the target object, a 3D volume image in which not only a structure of the target object but also attributes of the target object, such as a texture of the target object, are reflected may be acquired using attribute information corresponding to each pixel, which is acquired (or determined) via analysis of the attribute information.

Figure 12:
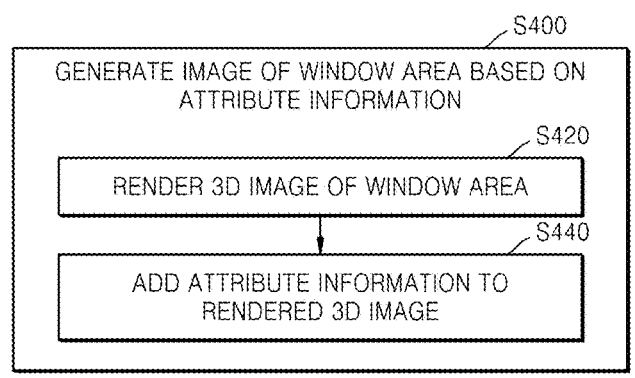
FIG. 12 is a flowchart of an operation of generating the image of the window area based on the attribute information according to another embodiment of the present invention.

FIG. 12 is a flowchart of an operation of generating the image of the window area based on the attribute information, according to another embodiment of the present invention.

In the present embodiment, the operation S400 may include operation S420 of performing rendering to acquire a rendered 3D image of the window area of the target object and operation S440 of adding the attribute information to the rendered 3D image.

The rendered 3D image is acquired by performing 3D volume rendering on the window area, and the attribute information is added to the rendered 3D image, thereby acquiring the 3D image in which the attribute information is reflected.

In other words, a first image is generated by performing 3D volume rendering on the window area, a second image is generated based on attribute information that corresponds to the window area and is extracted from the ultrasound data, and the first image and the second image overlap with each other so that the attribute information may be added to the first image (namely, the rendered 3D image). Attribute information obtained by filtering via a predetermined image processing filter or the like may be added to the rendered 3D image to thereby acquire the 3D image in which the attribute information has been reflected.

Figure 13:
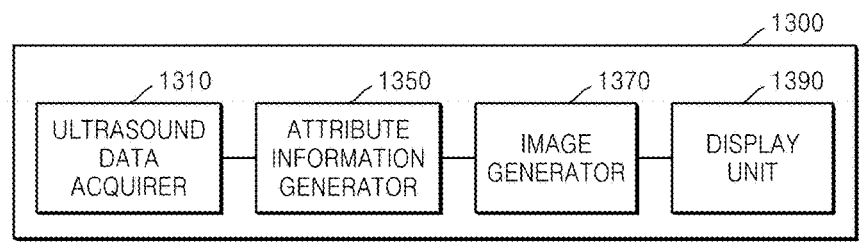
FIG. 13 is a block diagram of an apparatus for generating a 3D image in which attribute information of a target object is reflected, according to an embodiment of the present invention.

FIG. 13 is a block diagram of an apparatus 1300 for generating a 3D image in which attribute information of a target object is reflected, according to an embodiment of the present invention.

Referring to FIG. 13, the apparatus 1300 may include an ultrasound data acquirer 1310 acquiring ultrasound data of the target object, an attribute information generator 1350 generating the attribute information of the target object from the ultrasound data, and an image generator 1370 generating the 3D image of the target object based on the attribute information.

The apparatus 1300 may further include a display unit 1390 displaying the 3D image.

The attribute information may include at least one image attribute information selected from a spatial frequency, image intensity, an image histogram, a co-occurrence matrix, an LBP, and homogeneity of an ultrasound image of the target object.

The attribute information may include at least one selected from image attribute information, physical property information, and surface information of the target object.

The image generator 1370 may render the 3D image of the target object according to the attribute information generated by the attribute information generator 1350.

Figure 14:
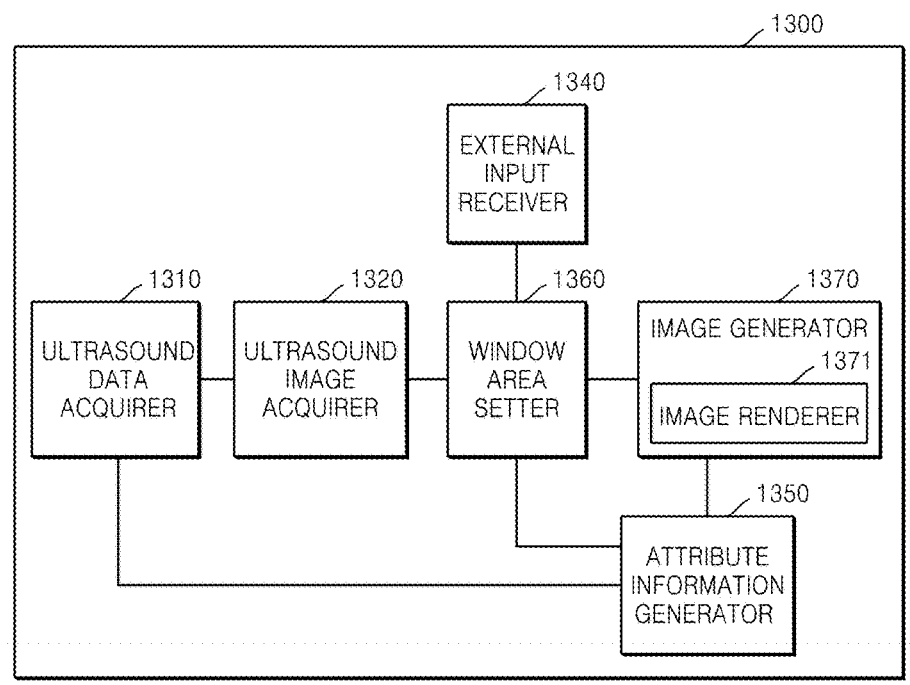
FIG. 14 is a block diagram of an apparatus for generating an image in which attribute information of a window area of a target object is reflected, according to an embodiment of the present invention.

FIG. 14 is a block diagram of an apparatus 1300 for generating an image in which attribute information of a window area of a target object is reflected, according to an embodiment of the present invention.

Referring to FIG. 14, the apparatus 1300 may include an ultrasound data acquirer 1310 acquiring ultrasound data of the target object, an ultrasound image acquirer 1320 acquiring an ultrasound image of the target object based on the ultrasound data, a window area setter 1360 setting the window area on the ultrasound image, an attribute information generator 1350 generating the attribute information of the target object from the ultrasound data, and an image generator 1370 generating the image of the window area based on the attribute information.

The window area setter 1360 may automatically set the window area to have a predetermined size to include a predetermined part of the target object. The predetermined size of area may be previously stored in a storage (not shown). For example, a predetermined window area having a predetermined size may be automatically set to include an upper part or a bottom curved side of the stomach of a patient.

The apparatus 1300 may further include an external input receiver 1340.

The window area setter 1360 may set a predetermined area on the ultrasound image acquired by the ultrasound image acquirer 1320, based on an external input received by the external input receiver 1340.

Image attribute information according to an embodiment of the present invention may include at least one selected from a spatial frequency, an image intensity, an image histogram, a co-occurrence matrix, an LBP, and homogeneity of an ultrasound image of a target object. Attribute information according to an embodiment of the present invention may include at least one selected from a texture of the target object and homogeneity of the target object.

The image generator 1370 may include an image renderer 1371 performing rendering to acquire the 3D image of the window area according to the attribute information generated by the attribute information generator 1350.

Figure 15:
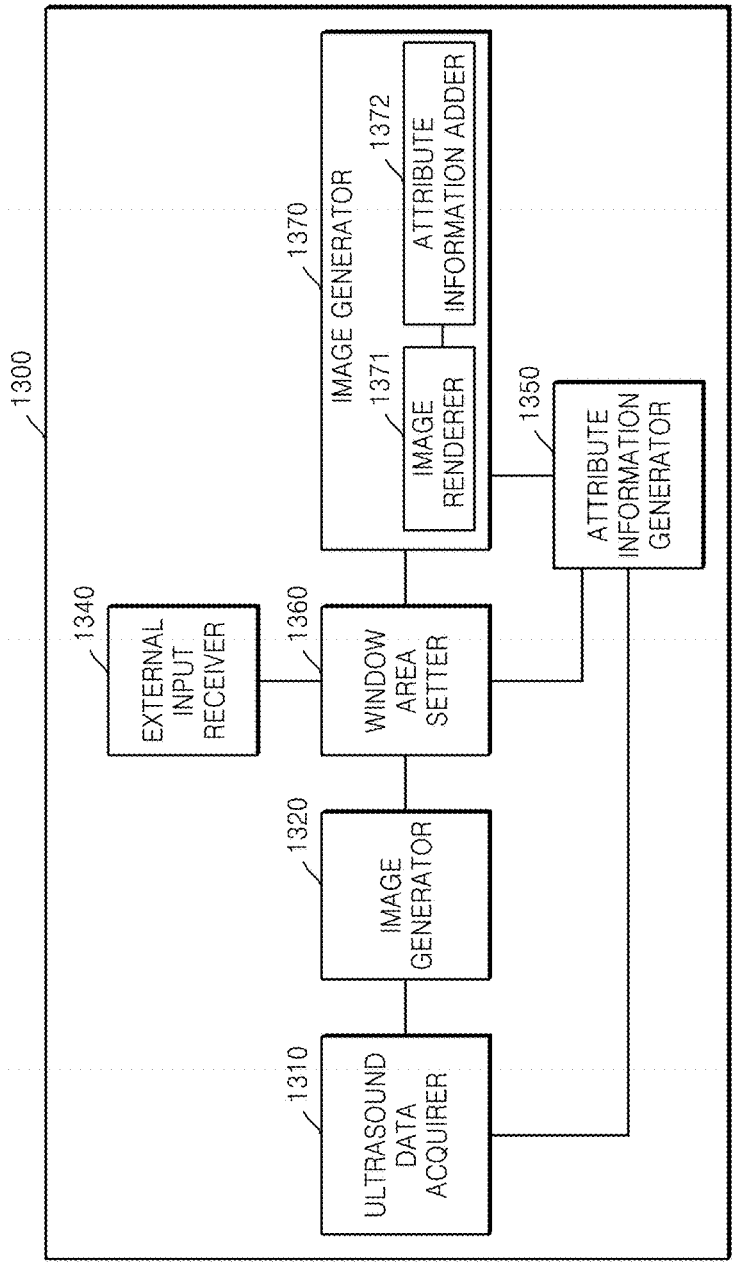
FIG. 15 is a block diagram of an apparatus for generating an image in which attribute information of a window area of a target object is reflected, according to another embodiment of the present invention.

FIG. 15 is a block diagram of an apparatus 1300 for generating an image in which attribute information of a window area of a target object is reflected, according to another embodiment of the present invention.

Referring to FIG. 15, an image generator 1370 may include an image renderer 1371 performing rendering to acquire a rendered 3D image of the window area and an attribute information adder 1372 adding the attribute information generated by the attribute information generator 1350 to the rendered 3D image.

Based on the attribute information generated by the attribute information generator 1350, the image generator 1370 may generate an attribute information image whereon the attribute information is displayed.

In other words, the rendered 3D image is acquired by performing 3D volume rendering on the window area, and the attribute information is added to the rendered 3D image, thereby acquiring the 3D image in which the attribute information is reflected.

The attribute information adder 1372 may overlap a first image generated by the image render 1371 with a second image (for example, the attribute information image) generated by the image generator 1370 to add the attribute information to the first image (namely, the rendered 3D image). The attribute information adder 1372 may include a predetermined image processing filter (not shown) or the like. In other words, the attribute information adder 1372 may add attribute information obtained by filtering via the predetermined image processing filter or the like to the rendered 3D image to thereby acquire the 3D image in which the attribute information is reflected.

FIGS. 16A-16C and 17A-17C are views for describing a reflection light effect as attribute information of a target object, according to an embodiment of the present invention.

Figure 16A:
FIGS. 16A-16C and 17A-17C are views for describing a reflection light effect as attribute information of a target object, according to an embodiment of the present invention.
Figure 16B:
Figure 16C:
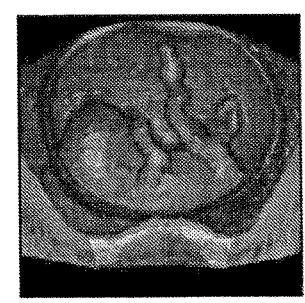

Referring to FIGS. 16A-16C and 17A-17C, an image of FIG. 16C may be generated by synthesizing an image of FIG. 16A and an image of FIG. 16B. A reflection light effect as shown in FIG. 16B may vary according to the properties of a target object.

For example, the apparatus 1300 of FIG. 13 may acquire the 3D image of FIG. 16A and attribute information corresponding to the image of FIG. 16B. For example, the apparatus 1300 of FIG. 13 may generate the image of FIG. 16C by adding the image of FIG. 16B to the 3D image of FIG. 16A. Accordingly, the apparatus 1300 of FIG. 13 may additionally render a reflection light effect that is the attribute information corresponding to the image of FIG. 16B, to the 3D image of FIG. 16A.

Figure 17A:
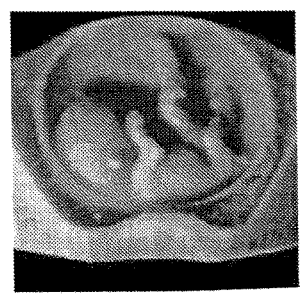
Figure 17B:
Figure 17C:
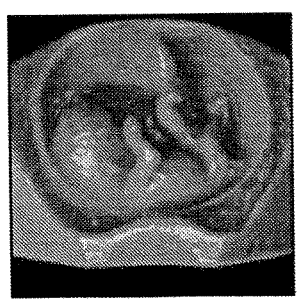

An image of FIG. 17C may be generated by synthesizing an image of FIG. 17A and an image of FIG. 17B. A reflection light effect as shown in FIG. 17B may vary according to the properties of a target object.

For example, the apparatus 1300 of FIG. 13 may acquire the 3D image of FIG. 17A and attribute information corresponding to the image of FIG. 17B. For example, the apparatus 1300 of FIG. 13 may generate the image of FIG. 17C by adding the image of FIG. 17B to the 3D image of FIG. 17A. Accordingly, the apparatus 1300 of FIG. 13 may additionally render the reflection light effect that is the attribute information corresponding to the image of FIG. 17B, to the 3D image of FIG. 17A.

Figure 18:
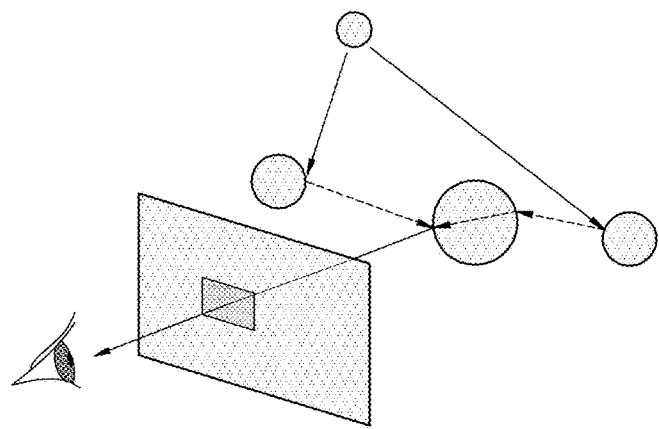
FIG. 18 is a schematic diagram for describing a method of obtaining ultrasound images of FIGS. 16A-16C and 17A-17C.

FIG. 18 is a schematic diagram for describing a method of obtaining the images of FIGS. 16A-16C and 17A-17C.

Referring to FIG. 18, a reflection light effect may be generated via 3D rendering. Specular rendering for generating a reflection light effect may be implemented by using ray tracing rendering. Ray tracing rendering uses a general lighting model. In other words, ray tracing rendering is a method of calculating a lighting effect due to reflection, refraction, absorption, and self-emission occurring when light strikes a surface of a target object, by tracing a path of light of all pixels on a screen when it is assumed that light is radiated from a camera. In ray tracing rendering, a local lighting model is used to calculate a lighting effect due to reflection between a light source and a target object. The local lighting model calculates lighting effects due to an ambient light effect, diffusive reflection, and reflection light effect. A reflection light effect among them is a lighting effect when a target object is highlighted by, in particular, light regularly reflected from a surface of a target object. The intensity of such a highlight varies according to the positions of a camera.

The reflection light effect may be calculated by Equation 1.

$$C_o = C_p K_s O_s (\vec{R} \cdot \vec{S})^n$$ [Equation 1]

$C_o$: Color of pixel
$C_p$: Specular light color
$K_s$: Specula reflection coefficient
$O_s$: Target object color
R: Reflection light vector
S: View vector
n: Specular reflection exponent The specular light color $C_p$ may denote the color of light for providing a reflection light effect. The specula reflection coefficient $K_s$ may denote the reflection degree of reflection light. The reflection light vector R may represent both the direction of reflection light and the intensity thereof. The view vector S may represent a unit vector for the direction of a view.

When the direction of the reflection light vector R and that of the view vector S are made the same in Equation 1, Equation 2 may be obtained.

In other words, a reflection light effect may also be calculated by using Equation 2 below. Supposing that the position and direction of a light source are not changed, the position and direction of the light source may be considered identical to those of a camera.

$$C_o = C_p K_s O_s (Rz)^N$$ [Equation 2]

$C_o$: Color of pixel
$C_p$: Specular light color
$K_s$: Specula reflection coefficient
$O_s$: Target object color
Rz: Z-axis (origin of view plane) value of a reflection vector when light is reflected from the surface of a target object
N: Specular reflection exponent The specular light color $C_p$, the specula reflection coefficient $K_s$, and the target object color $O_s$ in Equations 1 and 2 may be changed by using the attribute information such as a spatial frequency, an image intensity, an image histogram, a co-occurrence matrix, an LBP, or homogeneity of the ultrasound data described above with reference to FIGS. 3-8.

The specular light color $C_p$, the specula reflection coefficient $K_s$, and the target object color $O_s$ in Equations 1 and 2 may also be changed by using attribute information such as a mean, a dispersion, a standard distribution, skewness, or kurtosis of ultrasound data B, C, D, and E.

The specular light color $C_p$, the specula reflection coefficient $K_s$, and the target object color $O_s$ in Equations 1 and 2 may be statistical values of a distance between voxels of a target object.

FIGS. 19A and 19B illustrate images in which different pieces of attribute information of a window area of a target object are respectively reflected according to specular light exponents, according to an embodiment of the present invention.

FIG. 19A is an ultrasound image of the target object when the specular light exponent N in Equation 2 is 10, and FIG. 19B is an ultrasound image of the target object when the specular light exponent N in Equation 2 is 40. Compared with the ultrasound image of FIG. 19B, the ultrasound image of FIG. 19A has a small specular light exponent, and thus a highlighted portion is wide on the ultrasound image of FIG. 19A.

FIGS. 20A and 20B illustrate images in which different pieces of attribute information of a window area of a target object have been respectively reflected according to specula reflection coefficients, according to an embodiment of the present invention.

FIG. 20A is an ultrasound image of the target object when the specula reflection coefficient $K_s$ in Equation 2 is 0.19, and FIG. 20B is an ultrasound image of the target object when the specula reflection coefficient $K_s$ in Equation 2 is 0.5. Compared with the ultrasound image of FIG. 20B, the ultrasound image of FIG. 20A has a small specula reflection coefficient, and thus a highlighted portion on the ultrasound image of FIG. 20A is relatively weak.

Figure 21:
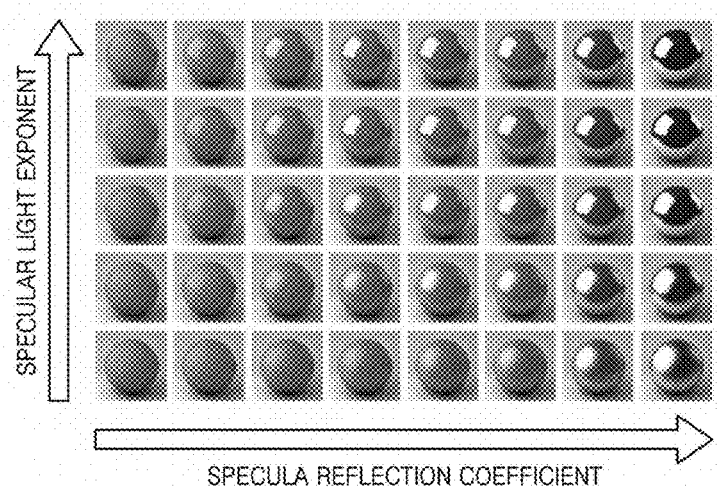
FIG. 21 illustrates a change in an image according to a specular light exponent and a specula reflection coefficient.

FIG. 21 illustrates a change in an image according to a specular light exponent and a specula reflection coefficient.

Referring to FIG. 21, as the specula reflection coefficient increases, the amount of reflected light increases. As the specular light exponent increases, the size of a portion of the image from which light is reflected decreases.

Figure 22A:
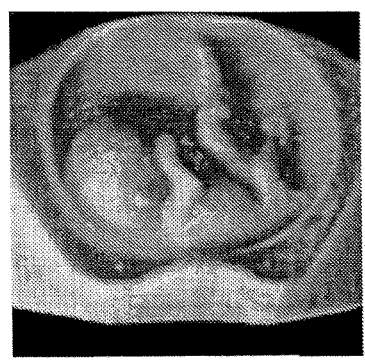
FIGS. 22A and 22B illustrate ultrasound images for explaining a reflection light effect when two light sources are used, according to an embodiment of the present invention.
Figure 22B:
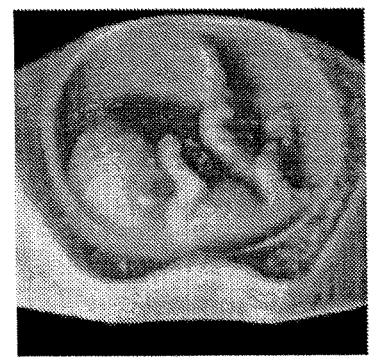

FIGS. 22A and 22B illustrate ultrasound images for explaining a reflection light effect when two light sources are used, according to an embodiment of the present invention.

FIG. 22A is an ultrasound image obtained by using only a single white light source. FIG. 22B is an ultrasound image obtained by using a white light source and a red light source. Compared with the ultrasound image of FIG. 22A, highlighted parts on the ultrasound image of FIG. 22B are redder.

When two light sources are used, the pixel color $C_o$ may be calculated by using Equation 3:

$$C_o = O_{s1}C_{p1}k_{s1}Rz_1^{n1} + \ldots + O_{sj}C_{pj}k_{sj}Rz_j^{nj} \quad \text{[Equation 3]}$$

In general, when the color of each target object ($O_{s1}$ through $O_{sj}$) is constant, the pixel color $C_o$ may be calculated by using Equation 4:

$$C_o = O_s(C_{p1}k_{s1}Rz_1^{n1} + \ldots + C_{pj}k_{sj}Rz_j^{nj}) \quad \text{[Equation 4]}$$

$C_o$: Pixel color
$C_{p1}$ through $C_{pj}$: Specular light color of each light source
$K_{s1}$ through $K_{sj}$: Specula reflection coefficient of each light source
$O_{s1}$ through $O_{sj}$: Target object color
$R_{z1}$ through $R_{zj}$: A z-axis value of a reflection vector for each light source when light is reflected from the surface of a target object
n1 through nj: Specular light exponent of each light source Equation 3 may be applied according to various embodiments. For example, when the target object colors $O_{s1}$ through $O_{sj}$ in Equation 3 are the same and reflection coefficients of the light sources are also the same, the specula reflection coefficients $K_{s1}$ through $K_{sj}$ may have the same values.

Figure 23:
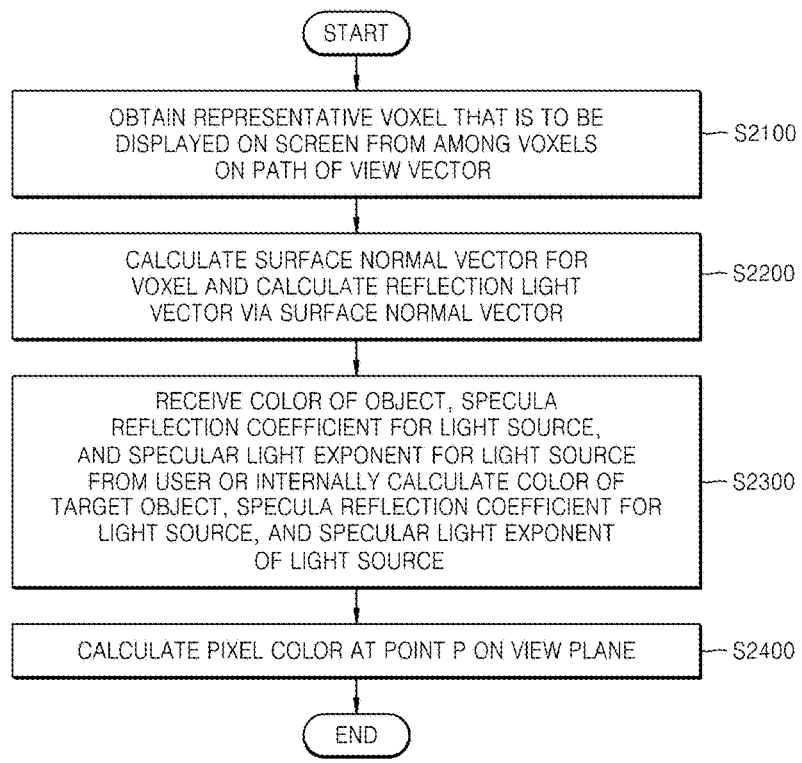
FIG. 23 is a flowchart of a 3D reflection light effect rendering method according to an embodiment of the present invention.

FIG. 23 is a flowchart of a 3D reflection light effect rendering method according to an embodiment of the present invention.

The image generator 1370 of FIG. 13 may generate an image according to the 3D reflection light effect rendering method of FIG. 23. Referring to FIG. 23, in operation S2100, the image generator 1370 may obtain a representative voxel V that is to be displayed on a screen from among voxels on a path of a view vector projected from a point P on a screen. In operation S2200, the image generator 1370 may calculate a surface normal vector for the voxel V and calculate a reflection light vector via the surface normal vector.

In operation S2300, the image generator 1370 may receive the specular light color $C_p$, the specula reflection coefficient $K_s$, and the target object color $O_s$ from a user or may internally calculate the specular light color $C_p$, the specula reflection coefficient $K_s$, and the target object color $O_s$. For example, the image generator 1370 may calculate the specular light color $C_p$, the specula reflection coefficient $K_s$, and the target object color $O_s$ by using the attribute information such as a spatial frequency, an image intensity, an image histogram, a co-occurrence matrix, an LBP, or homogeneity of the ultrasound data described above with reference to FIGS. 3-8.

In operation S2400, the image generator 1370 may calculate a pixel color $C_o$ at the point P on the screen via Equation 1 by using the specular light color $C_p$, the specula reflection coefficient $K_s$, the target object color $O_s$, and the reflection light vector.

The image renderers 1371 of FIGS. 14 and 15 may generate images according to the 3D reflection light effect rendering method of FIG. 23.

Figure 24:
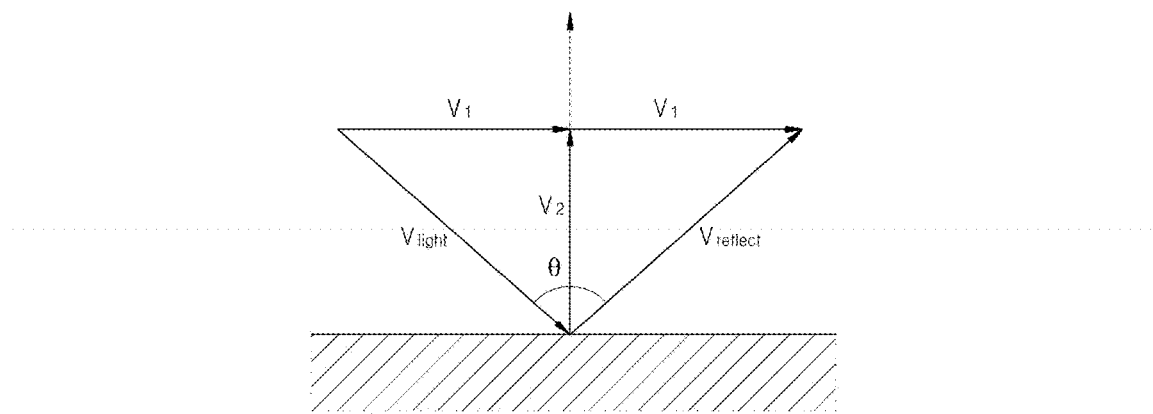
FIG. 24 is a view for illustrating a method of calculating a reflection light vector via a normal vector.

FIG. 24 is a view for illustrating a method of calculating a reflection light vector $V_{reflect}$ via a normal vector $V_{normal}$.

Referring to FIG. 24, the image generator 1370 may calculate the reflection light vector $V_{reflect}$ by using Equation 5.

$$\begin{aligned}
\overrightarrow{v_{reflect}} &= 2\overrightarrow{v_1} - \overrightarrow{v_{light}} \quad \text{[Equation 5]} \\
&= 2(\overrightarrow{v_{light}} + \overrightarrow{v_2}) - \overrightarrow{v_{light}} \\
&= \overrightarrow{v_{light}} + 2\overrightarrow{v_2} \\
&= \overrightarrow{v_{light}} - 2\frac{\overrightarrow{v_{light}} \cdot \overrightarrow{v_{normal}}}{|v_{light}||v_{normal}|}\overrightarrow{v_{normal}}
\end{aligned}$$

The image generator 1370 may calculate the reflection light vector $V_{reflect}$ via the normal vector $V_{normal}$ and a light source vector $V_{light}$ by using Equation 5.

Figure 25:
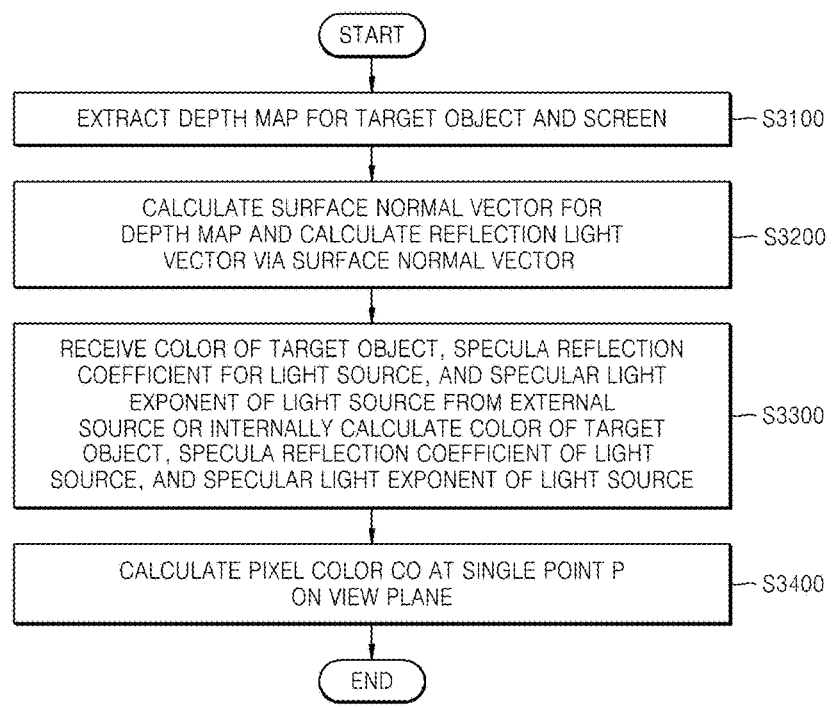
FIG. 25 is a flowchart of a 3D reflection light effect rendering method according to an embodiment of the present invention.

FIG. 25 is a flowchart of a 3D reflection light effect rendering method according to an embodiment of the present invention.

The image generator 1370 of FIG. 13 may generate an image according to the 3D reflection light effect rendering method of FIG. 25. Referring to FIG. 25, in operation S3100, the image generator 1370 extracts a depth map for a target object and a screen. In operation S3200, the image generator 1370 may calculate a surface normal vector and a reflection light vector for the depth map. In operation S3300, the image generator 1370 may receive the specular light color $C_p$, the specula reflection coefficient $K_s$, and the target object color $O_s$ from an external source or may internally calculate the specular light color $C_p$, the specula reflection coefficient $K_s$, and the target object color $O_s$. In operation S3400, the image generator 1370 may calculate a pixel color $C_o$ at a single point P on the screen via Equation 2 by using the specular light color $C_p$, the specula reflection coefficient $K_s$, the target object color $O_s$, and the reflection light vector.

Figure 26:
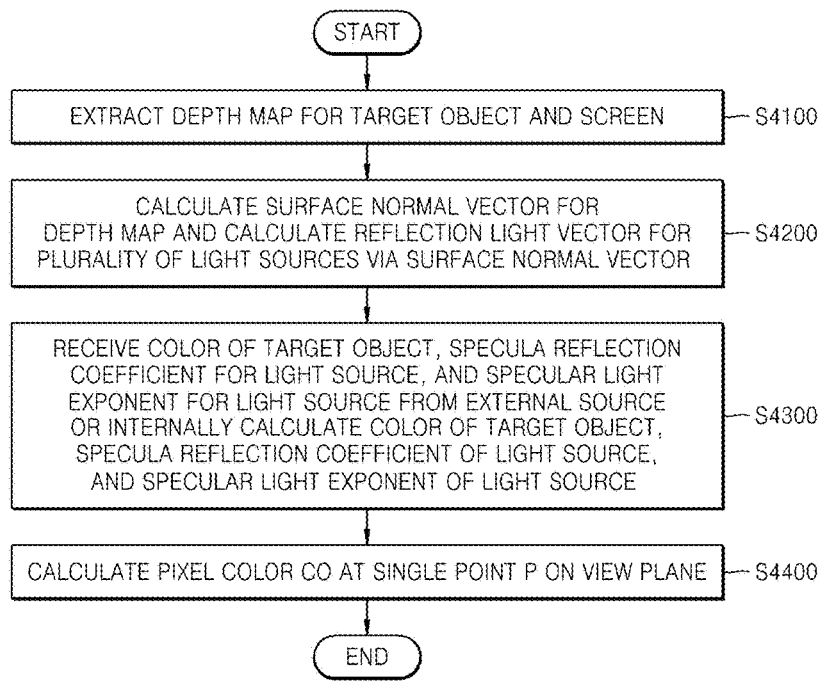
FIG. 26 is a flowchart of a 3D reflection light effect rendering method according to an embodiment of the present invention.

FIG. 26 is a flowchart of a 3D reflection light effect rendering method according to an embodiment of the present invention.

The image generator 1370 of FIG. 13 may generate an image according to the 3D reflection light effect rendering method of FIG. 26. Referring to FIG. 26, in operation S4100, the image generator 1370 extracts a depth map for a target object and a screen. In operation S4200, the image generator 1370 may calculate a surface normal vector for depth map and calculate a reflection light vector for plurality of light sources via surface normal vector. In operation S4300, the image generator 1370 may receive the specular light color $C_p$, the specula reflection coefficient $K_s$, and the target object color $O_s$ from an external source or may internally calculate the specular light color $C_p$, the specula reflection coefficient $K_s$, and the target object color $O_s$. In operation S4400, the image generator 1370 may calculate a pixel color $C_o$ at a single point P on the screen via Equation 3 or 4 by using the specular light color $C_p$, the specula reflection coefficient $K_s$, the target object color $O_s$, and the reflection light vector.

Each of the 3D reflection light effect rendering methods of FIGS. 24, 25, and 26 may be performed in the operation S500 of FIG. 10. Each of the 3D reflection light effect rendering methods of FIGS. 24, 25, and 26 may be performed by the image generator 1370 of FIG. 13, the image renderer 1371 of FIG. 14, or the image renderer 1371 of FIG. 15.

Each of the 3D reflection light effect rendering methods of FIGS. 24, 25, and 26 may be performed together with grey scale rendering and diffused light rendering. Alternatively, each of the 3D reflection light effect rendering methods of FIGS. 24, 25, and 26 may be performed independently from grey scale rendering and diffused light rendering, and rendered images obtained by the 3D reflection light effect rendering method, the grey scale rendering, and the diffused light rendering may be synthesized into an image.

Figure 27:
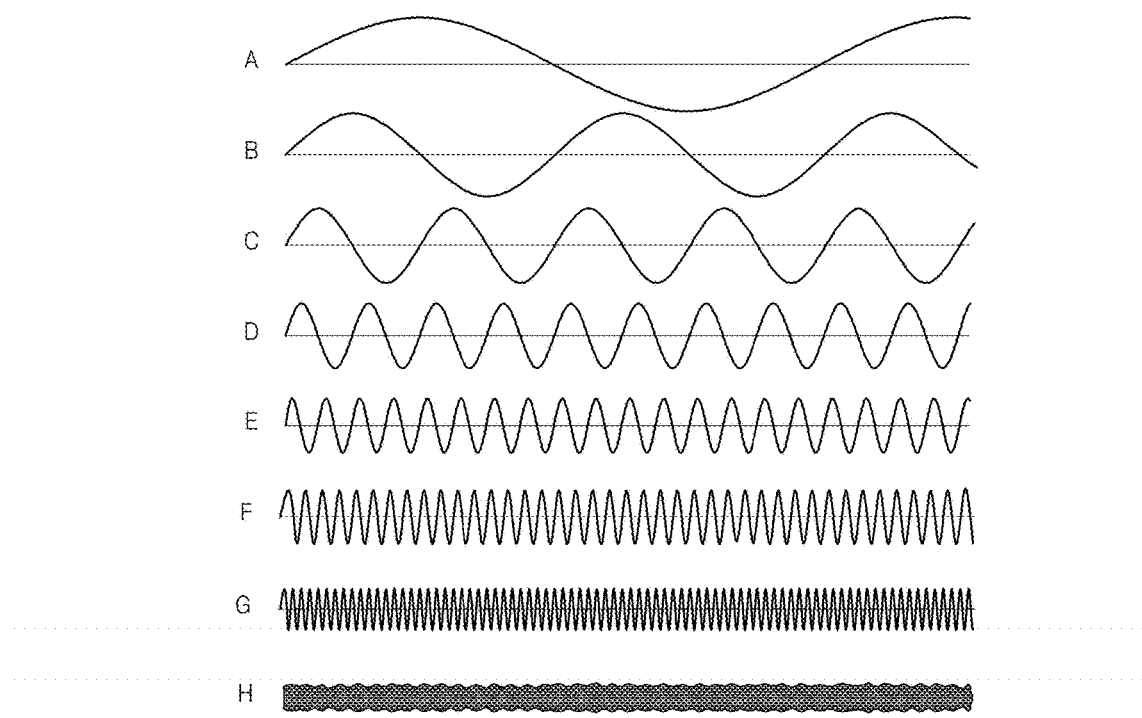
FIGS. 27 through 29 are views for describing a method of calculating surface information of a target object.
Figure 28:
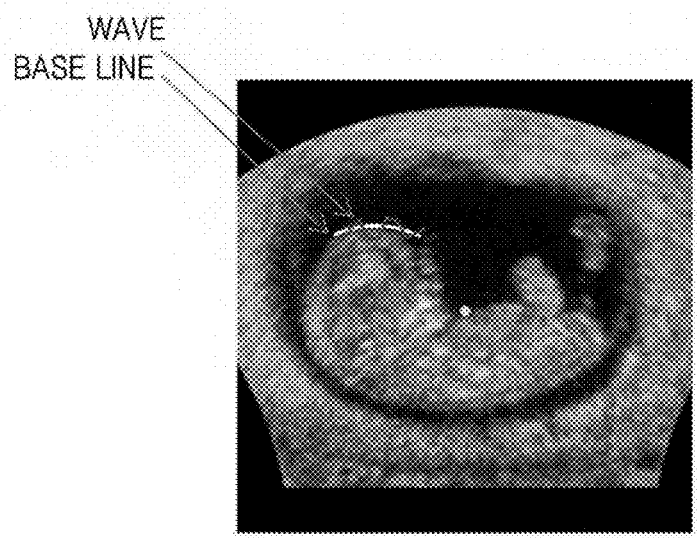
Figure 29:

FIGS. 27 through 29 are views for describing a method of calculating surface information of a target object, according to an embodiment of the present invention.

Referring to FIG. 27, when the surface of the target object is expressed using a geometrical model, various ways, for example, waves A through H, may be used. Each of the waves A through H has a base line. The base line is a basis for a wave. The base line may be calculated from a wave via smoothing and line fitting.

If the number of times the wave and the basis line intersect increases, the surface of the target object may be considered rough. If the number of times the wave and the basis line intersect decreases, the surface of the target object may be considered smooth. Accordingly, a wave may express a smoother surface of the target object in a direction from the wave H to the wave A, and also, a wave may express a rougher surface of the target object in a direction from the wave A to the wave H.

Referring to FIG. 28, the surface information of the target object may be calculated from a 2D image (or a cross-section of a 3D ultrasound volume image) of the target object by using a wave and a base line. When the surface information of the target object is calculated from the 2D image of the target object, various shapes of waves and base lines may be used instead of the waves and base lines of FIG. 27. For example, a base line may be curved as illustrated in FIG. 28.

Referring to FIG. 29, the waves and base lines of FIG. 27 may be expanded into a 3D ultrasound volume to define a wave surface and a base surface. When a 2D image of FIG. 28 is expanded into a 3D image, a 3D image of FIG. 29 may be obtained. In the method according to the present embodiment, a wave surface and a base surface of the 3D image may be calculated from the waves and base lines of the 2D image.

The descriptions of the above-described methods may be applied to the apparatuses 1300 of FIGS. 13-15. Therefore, contents of the apparatuses 1300 that are the same as those of the above-described methods will not be described herein.

The embodiments of the present invention can be written as computer programs and can be implemented in general-use digital computers that execute the programs using a computer readable recording medium.

Examples of the computer readable recording medium include magnetic storage media (e.g., ROM, floppy disks, hard disks, etc.), optical recording media (e.g., CD-ROMs, or DVDs), etc.

The exemplary embodiments should be considered in descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of generating a three-dimensional (3D) image of a target object, the method comprising:
   acquiring ultrasound data of the target object; and
   generating the 3D image of the target object by using the ultrasound data,
   so that a part of the target object having attribute information different than attribute information of other parts of the target object is shown on the 3D image differently than the other parts,
   wherein the generating of the 3D image of the target object comprises:
   generating a first 3D image of the target object by 3D volume rendering; and
   generating the 3D image of the target object to express information about a structure and a texture of the target object by synthesizing the first 3D image and an attribute information image having a reflection light effect according to the texture of the target object.

2. The method of claim 1, wherein the generating of the 3D image is performed by using at least one selected from a specular reflection coefficient, a specular light exponent, and a color of the target object.

3. The method of claim 1, further comprising displaying the 3D image of the target object.

4. The method of claim 1, wherein the image having the reflection light effect is generated by a plurality of light sources.

5. An apparatus for generating a three-dimensional (3D) image of a target object, the apparatus comprising:
   an ultrasound data acquirer configured to acquire ultrasound data of the target object; and
   a computer configured to generate the 3D image of the target object by using the ultrasound data,
   so that a part of the target object having attribute information different than attribute information of other parts of the target object is shown on the 3D image differently than the other parts,
   wherein the computer is configured to generate a first 3D image of the target object by 3D volume rendering, and generate the 3D image of the target object to express information about a structure and a texture of the target object by synthesizing the first 3D image and an attribute information image having a reflection light effect according to the texture of the target object.

6. The apparatus of claim 5, wherein the computer generates the 3D image of the target object by using at least one selected from a specular reflection coefficient, a specular light exponent, and a color of the target object.

7. The apparatus of claim 5, further comprising a display unit configured to display the 3D image of the target object.

8. The apparatus of claim 5, wherein the image having the reflection light effect is generated by a plurality of light sources.

* * * * *